United States Patent
Somasundaram et al.

(10) Patent No.: US 10,916,008 B2
(45) Date of Patent: Feb. 9, 2021

(54) METHOD FOR AUTOMATIC TOOTH TYPE RECOGNITION FROM 3D SCANS

(71) Applicant: 3M INNOVATIVE PROPERTIES COMPANY, St. Paul, MN (US)

(72) Inventors: Guruprasad Somasundaram, Minneapolis, MN (US); Ravishankar Sivalingam, San Mateo, CA (US); Evan J. Ribnick, St. Louis Park, MN (US); Kevin S. Xu, Toledo, OH (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 262 days.

(21) Appl. No.: 16/018,115

(22) Filed: Jun. 26, 2018

(65) Prior Publication Data

US 2018/0300877 A1    Oct. 18, 2018

Related U.S. Application Data (62) Division of application No. 14/965,033, filed on Dec. 10, 2015, now Pat. No. 10,032,271.

(51) Int. Cl.
*G06T 7/00* (2017.01)
*G06K 9/00* (2006.01)
(Continued)

(52) U.S. Cl.
CPC .......... *G06T 7/0012* (2013.01); *A61B 5/0088* (2013.01); *A61C 9/0053* (2013.01); *G06K 9/00214* (2013.01); *G06K 9/32* (2013.01); *G06K 9/34* (2013.01); *G06K 9/4628* (2013.01); *G06K 9/628* (2013.01); *G06K 9/6267* (2013.01);
(Continued)

(58) Field of Classification Search
USPC .................................. 382/128; 433/155, 215
See application file for complete search history.

(56) References Cited

U.S. PATENT DOCUMENTS 6,685,469 B2    2/2004  Chishti et al.
7,040,896 B2    5/2006  Pavlovskaia et al.
(Continued)

FOREIGN PATENT DOCUMENTS

WO    WO 2015/141760    9/2015

OTHER PUBLICATIONS

Prajapati et al., "A Simple and Novel CBIR Technique for Features Extraction Using AM Dental Radiographs," Communication Systems and Network Technologies, 2012 International Conference on IEEE, pp. 198-202, May 11, 2012.
(Continued)

*Primary Examiner* — Ishrat I Sherali (57) ABSTRACT

Methods for recognizing or identifying tooth types using digital 3D models of teeth. The methods include receiving a segmented digital 3D model of teeth and selecting a digital 3D model of a tooth from the segmented digital 3D model. An aggregation of the plurality of distinct features of the tooth is computed to generate a single feature describing the digital 3D model of the tooth. A type of the tooth is identified based upon the aggregation, which can include comparing the aggregation with features corresponding with known tooth types. The methods also include identifying a type of tooth, without segmenting it from an arch, based upon tooth widths and a location of the tooth within the arch.

18 Claims, 8 Drawing Sheets

(51) Int. Cl.
*G06K 9/46* (2006.01)
*G06K 9/62* (2006.01)
*G06K 9/34* (2006.01)
*A61B 5/00* (2006.01)
*A61C 9/00* (2006.01)
*G06K 9/66* (2006.01)
*G06K 9/32* (2006.01)

(52) U.S. Cl.
CPC .............. *G06K 9/6271* (2013.01); *G06K 9/66* (2013.01); *G06K 2209/055* (2013.01); *G06T 2207/10012* (2013.01); *G06T 2207/30036* (2013.01)

(56) References Cited

U.S. PATENT DOCUMENTS

| | | |
|---|---|---|
| 7,134,874 B2 | 11/2006 | Chishti et al. |
| 7,605,817 B2 | 10/2009 | Zhang et al. |
| 7,956,862 B2 | 6/2011 | Zhang et al. |
| 8,108,189 B2 | 1/2012 | Chelnokov et al. |
| 8,135,569 B2 | 3/2012 | Matov et al. |
| 8,170,327 B2 | 5/2012 | Glor et al. |
| 8,194,067 B2 | 6/2012 | Raby et al. |
| 8,422,283 B2 | 4/2013 | Chang |
| 9,626,462 B2 | 4/2017 | Somasundaram et al. |
| 10,032,271 B2 * | 7/2018 | Somasundaram ....... G06K 9/66 |
| 2003/0068079 A1 | 4/2003 | Park |
| 2004/0197727 A1 | 10/2004 | Sachdeva et al. |
| 2007/0168152 A1 * | 7/2007 | Matov .................... B33Y 80/00 702/155 |
| 2008/0154419 A1 * | 6/2008 | Cheng ...................... G06T 7/60 700/118 |
| 2009/0246726 A1 | 10/2009 | Chelnokov et al. |
| 2013/0282351 A1 | 10/2013 | Tank |
| 2014/0172375 A1 * | 6/2014 | Grove ................. A61C 9/0053 703/1 |
| 2016/0004811 A1 | 1/2016 | Somasundaram et al. |
| 2018/0360567 A1 * | 12/2018 | Xue ....................... A61C 7/002 |
| 2020/0000554 A1 * | 1/2020 | Makarenkova ........ G16H 30/20 |

OTHER PUBLICATIONS

Kondo et al., "Robust Arch Detection and Tooth Segmentation in 3D Images of Dental Plaster Models," Medical Imaging and Augmented Reality, pp. 241-246, Jun. 2001.

Laurendeau et al., "A Computer-Vision Technique for the Acquisition and Processing of 3-D Profiles of Dental Imprints: An Application in Orthodontics," IEEE Transactions on Medical Imaging, vol. 10, No. 3, pp. 453-461, Sep. 1991.

Wu, Kan et al., "Tooth segmentation on dental meshes using morphologic skeleton," Computers and Graphics, vol. 38, pp. 199-211, Feb. 1, 2014.

Mahoor, M.H. et al., "Classification and numbering of teeth in dental bitewing images," Pattern Recognition, vol. 38, no. 4, pp. 577-586, Apr. 1, 2005.

Lin, P.L. et al., "An effective classification and numbering system for dental bitewing radiographs using teeth region and contour information," Pattern Recognition, vol. 43, No. 4, pp. 1380-1392, Apr. 1, 2010.

Belongie, "Shape Matching and Object Recognition Using Shape Contexts," IEEE Transactions on Pattern Analysis and Machine Intelligence, Apr. 2002, vol. 24, No. 24, pp. 509-522.

Fisher, "The Use of Multiple Measurements in Taxonomic Problems," Annals of Eugenics, Sep. 1936, vol. 7, No. 2, pp. 179-188.

Hassan, "Influence of scanning and reconstruction parameters on quality of three-dimensional surface models of the dental arches from cone beam computed tomography," Clinical Oral Investigations, 2010, vol. 14, pp. 303-310.

Johnson, "Spin-Images: A Representation for 3-D Surface Matching," (1997).

Kalogerakis, "Learning 3D Mesh Segmentation and Labeling," Siggraph, Jul. 2010, vol. 29, No. 3, 13 pages.

Sivalingam, "Tensor Sparse Coding for Positive Definite Matrices," IEEE Transactions on Pattern Analysis and Machine Intelligence, Mar. 2014, vol. 36, No. 3, pp. 592-605.

* cited by examiner

METHOD FOR AUTOMATIC TOOTH TYPE RECOGNITION FROM 3D SCANS

BACKGROUND

Intra-oral scanners can provide for 3D scanned meshes of teeth. Those digital 3D models of teeth can be used in a partially automated digital workflow, which performs an interactive segmentation of teeth but requires human input to label the individual teeth by tooth type. Sometimes, the human operator might mislabel a tooth, which could result in errors in the digital workflow. Accordingly, a need exists for an automated tooth identification and labeling feature in the software of a digital workflow, or in other applications.

SUMMARY

A method for identifying a tooth type, consistent with the present invention, includes receiving a segmented digital 3D model of teeth and selecting a digital 3D model of a tooth from the segmented digital 3D model. The selected digital 3D model is associated with a plurality of distinct features. The method also includes computing an aggregation of the plurality of distinct features to generate a single feature describing the digital 3D model of the tooth and identifying a type of the selected digital 3D model of the tooth based upon the aggregation.

Another method for identifying a tooth type, consistent with the present invention, includes, receiving a digital 3D model of an arch of teeth and determining widths of teeth within the digital 3D model of the arch. The method also includes identifying types of teeth in the digital 3D model of arch based upon the determined widths and locations of the teeth in the arch.

A method for interstice detection of teeth, consistent with the present invention, includes receiving a digital 3D model of an arch of teeth and determining widths of teeth within the digital 3D model of the arch. The method also includes using the determined widths to detect and identify interstices between teeth within the digital 3D model of the arch, which can be used to help or improve upon a segmentation of the model.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Embodiments of the present invention include an approach to recognize or identify the tooth type of a given tooth by computing shape features from the 3D scanned surface mesh of the tooth. The approach includes use of a classifier that can discriminate between the 32 different tooth types. In one approach, the input to the algorithm is a segmented individual tooth, and the 3D mesh is processed to extract different shape features at each vertex on the mesh. The shape features over the entire tooth are consolidated into a single covariance matrix, which is then used as the input to a classification algorithm. Since the covariance of the features is used, this approach is robust to the orientation and alignment of the tooth scan. Alternatively, other forms of aggregation with desirable properties can be used, for example feature averaging, feature histograms, sparse coding of features, bag of features, or others. In another approach not using segmentation, teeth within a digital 3D model of an arch are identified based upon tooth widths and locations within the arch.

The thirty-two different tooth types comprise the following for each of the four quadrants—upper left, upper right, lower left, and lower right: central incisor; lateral incisor; canine; first premolar; second premolar; first molar; second molar; and third molar. The present method can also be used for the twenty primary teeth. The tooth recognition and identification can involve predicting the type of tooth or identifying the type of tooth with a particular degree of accuracy of the actual type for the tooth where the degree of accuracy is high enough for the identification of tooth type to be useful. For example, the identifying can include identifying a type of tooth with 90%, or 95%, or 99% accuracy.

Tooth Recognition of Segmented Scan

Figure 1:
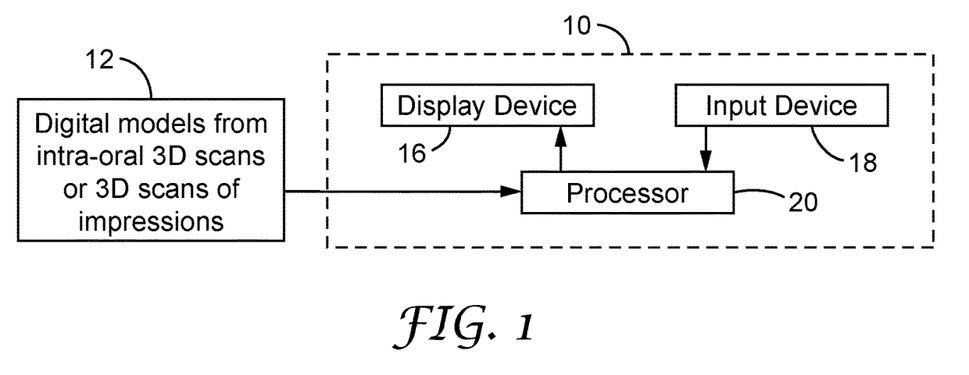
FIG. 1 is a diagram of a system for predicting or identifying tooth types, or determining tooth width distributions, using a digital 3D model based upon intra-oral 3D scans or 3D scans from impressions.
Figure 2:
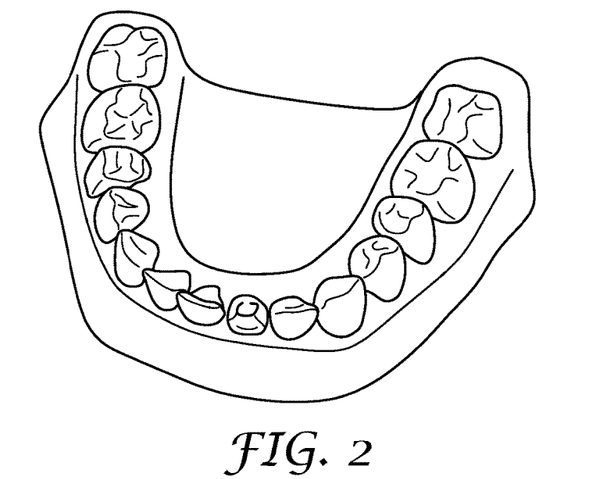
FIG. 2 illustrates a 3D model of teeth from intra-oral scans.

FIG. 1 is a diagram of a system 10 for predicting or identifying tooth types using a digital 3D model based upon intra-oral 3D scans. System 10 includes a processor 20 receiving digital 3D models of teeth (12) from intra-oral 3D scans or scans of impressions of teeth. System 10 can also include an electronic display device 16, such as a liquid crystal display (LCD) device, for displaying indications of tooth types and corresponding shapes, and an input device 18 for receiving user commands or other information. An example of digital 3D model of a patient's teeth from a scan is illustrated in FIG. 2. Systems to generate digital 3D images or models based upon image sets from multiple views are disclosed in U.S. Pat. Nos. 7,956,862 and 7,605, 817, both of which are incorporated herein by reference as if fully set forth. These systems can use an intra-oral scanner to obtain digital images from multiple views of teeth or other intra-oral structures, and those digital images are processed to generate a digital 3D model representing the scanned teeth. System 10 can be implemented with, for example, a desktop, notebook, or tablet computer. System 10 can receive the 3D scans locally or remotely via a network.

Figure 4:
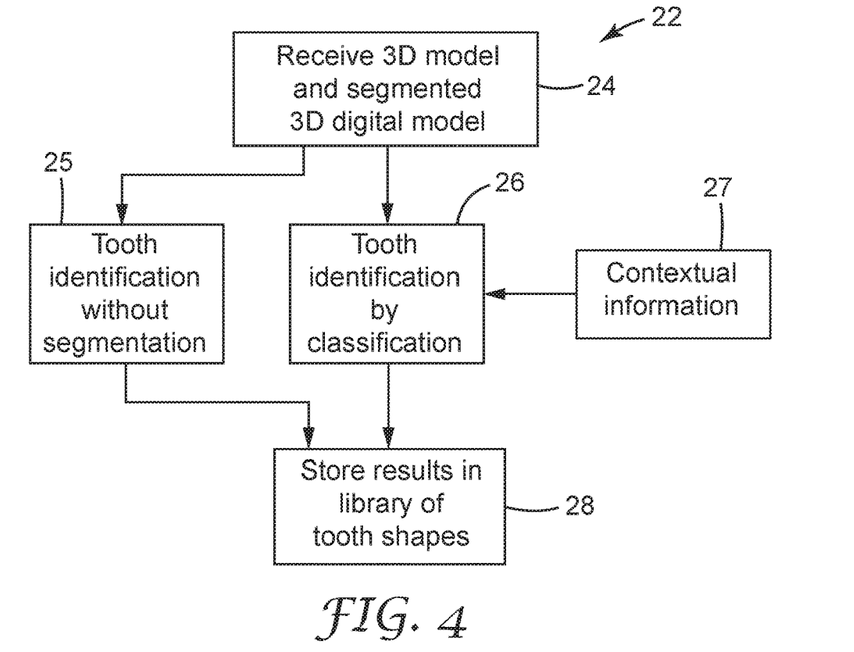
FIG. 4 is a flow chart of a method for tooth identification using a digital 3D model.

FIG. 4 is a flow chart of a method 22 for predicting or identifying tooth types in a digital 3D model. Method 22 can be implemented in software or firmware modules, for example, for execution by processor 20. Method 22 can alternatively be implemented in hardware modules or a combination of software and hardware.

Method 22 includes receiving a segmented digital 3D model of a patient's teeth (step 24) and identifying the tooth type by classification of the aggregated features of the tooth (step 26), which can also include receiving contextual information (step 27) for use in identifying the type of tooth. The tooth identification can also be performed by receiving the 3D model or an arch within the model (step 24) and identifying the tooth type without segmentation of the 3D model (step 25). The results of the tooth identification are stored in an electronic library of tooth shapes (step 28)

Figure 3:
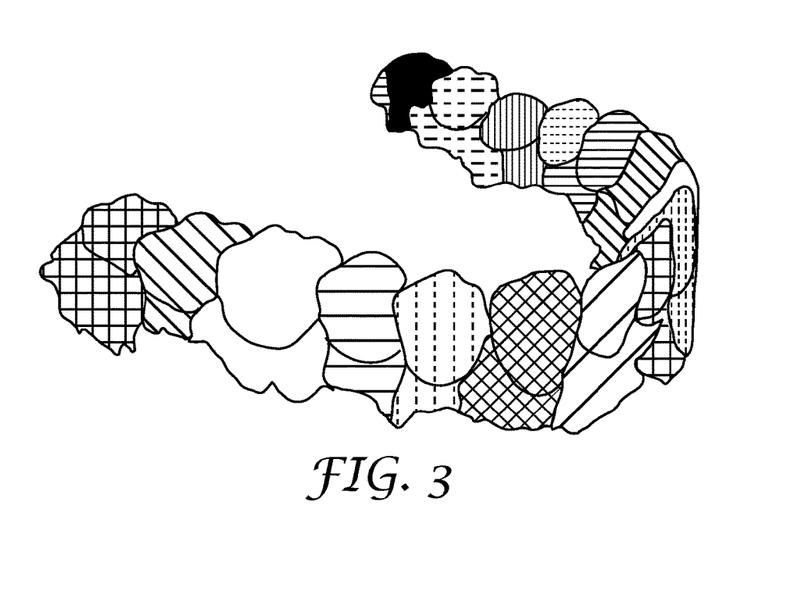
FIG. 3 illustrates a 3D model of teeth segmented to digitally separate each tooth.

The input to method 22 is a 3D model or a segmented digital 3D model, as recited in step 24, and a particular digital 3D model of a tooth from the segmented model can be selected for identification in step 26. An example of teeth that have been segmented in a digital model is illustrated in FIG. 3. The segmentation provides for separating individual teeth in the digital 3D model, as represented by the shading in FIG. 3, and each tooth in the model can essentially be digitally separated from the other teeth for further processing. The digital 3D model of teeth can be segmented in a variety of ways for input to method 22. In some cases, a software interface may be presented in order for a user to perform the segmentation, or some parts of it, manually. In other cases, the segmentation can be performed automatically through processing of the digital 3D model. Methods for performing such segmentation are disclosed in U.S. Pat. No. 9,626,462, which is incorporated herein by reference as if fully set forth.

Figure 5:
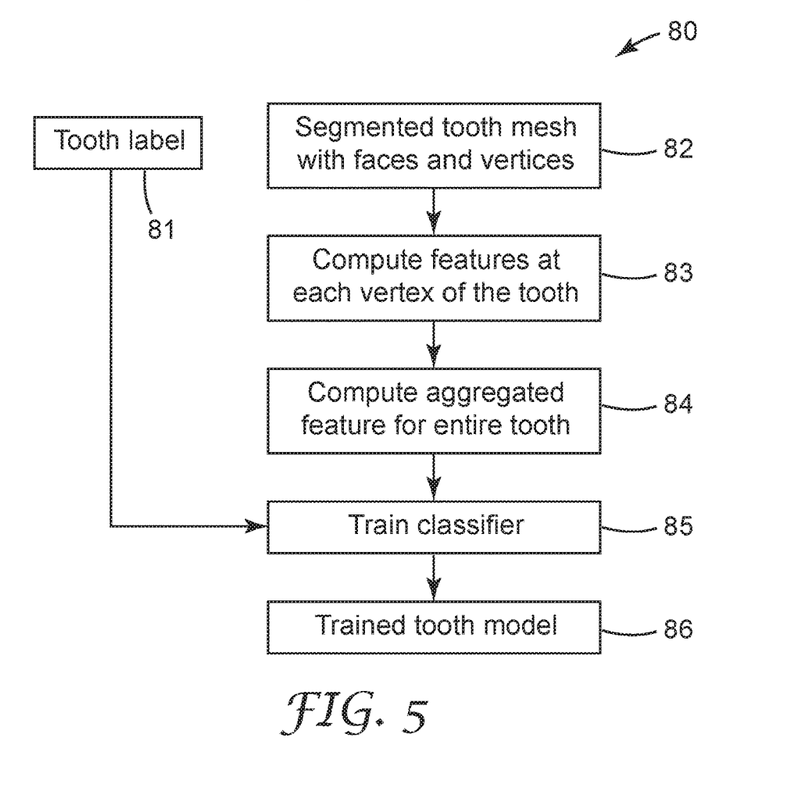
FIG. 5 is a flow chart of a training phase for a tooth classification method to identify tooth shapes.
Figure 6:
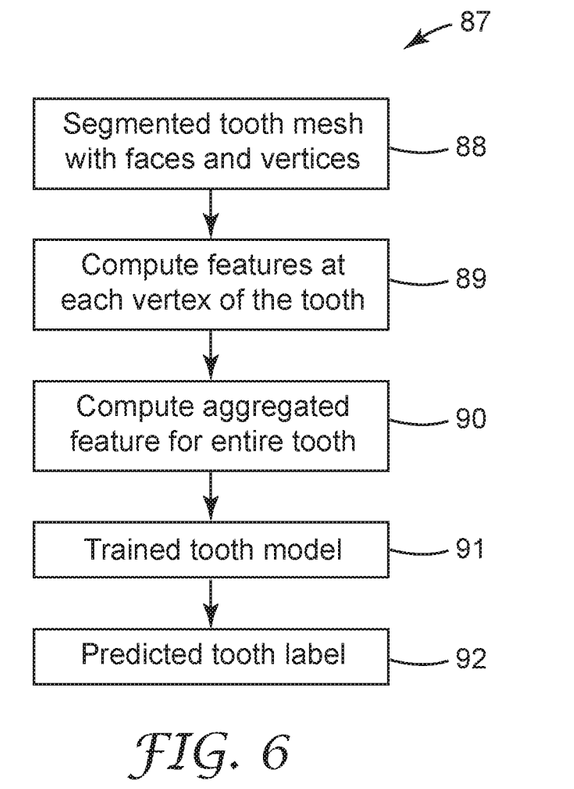
FIG. 6 is a flow chart of a test phase for the tooth classification method.

FIGS. 5 and 6 are flow charts of, respectively, a training phase method 80 and a test phase method 87 for the tooth identification by classification (step 26). Methods 80 and 87 can be implemented in software or firmware modules, for example, for execution by processor 20. Methods 80 and 87 can alternatively be implemented in hardware modules or a combination of software and hardware.

Method 80 for the training phase involves: receiving a segmented tooth mesh with faces and vertices (step 82); computing features at each vertex of the tooth (step 83); computing an aggregated feature for the entire tooth (step 84); training the classifier by associating a tooth label 81 with the computed aggregated feature (step 85); and providing the trained tooth model (step 86). Method 87 for the test phase involves: receiving a segmented tooth mesh with faces and vertices (step 88); computing features at each vertex of the tooth (step 89); computing an aggregated feature for the entire tooth (step 90); obtaining from the trained tooth model a label for the computed aggregated feature (step 91); and providing a predicted tooth label for the segmented tooth (step 92).

The steps of methods 80 and 87 for tooth identification by point classification (corresponding with step 26 in FIG. 4) can be implemented as follows. The 3D scans of teeth are represented as triangulated meshes, comprising faces and vertices. The triangular mesh is a common representation of 3D surfaces and has two components. The first component, referred to as the vertices of the mesh, are simply the coordinates of the 3D points that have been reconstructed on the surface—a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

Each vertex is represented by a 243-dimensional feature vector, comprising a combination of feature descriptors, namely: vertex coordinates; magnitude and direction of minimum and maximum curvature; mean-, absolute- and Gaussian-curvature; vertex normals; mesh local covariance and its eigenvalues and eigenvectors; spin image features; shape context features; principal component analysis (PCA) features; and mesh Fourier features. These features are consolidated into a 243-dimensional feature descriptor per vertex, including but not limited to these features. Any subset of these features, as well as optional additional features can also be used for tooth classification. Additional features can include tooth cross-sectional area, perimeter of a cross-section, tooth length, width, and height, surface area, volume, profiles as viewed along any dental plane (occlusal, facial, etc.), Radon transform features, bag-of-words descriptors, or other features.

To obtain a single feature describing an entire digitized tooth, the method computes the covariance matrix of the 243-dimensional vertex-wise features, yielding a 243×243 symmetric matrix. Since this matrix is symmetric, it only has 243×(243+1)/2=29,646 unique entries. Further, this matrix is positive definite, meaning that it has positive eigenvalues.

The mean vector is computed as:

$$\mu = \frac{1}{N}\sum_{i=1}^{N} x_i,$$

where $x_i$ is 243-dimensional feature vector at vertex i, and N is the number of vertices in the tooth mesh.

The covariance matrix is computed as $$C = \frac{1}{N}\sum_{i=1}^{N}(x_i - \mu)(x_i - \mu)^T$$

In order to convert this matrix feature into a vector feature for use in the classification step, the method computes the matrix logarithm of the covariance C, S=log m (C), where log m(.) represents the matrix logarithm. S is now a symmetric 243×243 matrix with no constraints on its eigenvalues. The method takes the upper triangular part of this matrix and converts it to a 29,646-dimensional feature vector. This high-dimensional feature vector now represents the entire tooth shape and structure of the tooth. Other forms of feature aggregation can also be used.

There are two possible ways to perform tooth classification, with each tooth sample being represented by the 29,646-dimensional feature vector. The method can learn an N-class, such as a 32-class, discriminative (or generative) classifier such as linear or kernel SVMs directly in the ambient high-dimensional space. The method can also, or alternatively, project these high-dimensional feature vectors corresponding to each tooth class to a lower-dimensional subspace, and learn a multi-class classifier in this subspace. This projection can be performed using Fisher Linear Discriminant Analysis, Principal Component Analysis, and other supervised or unsupervised dimensionality reduction techniques. Once the tooth type is identified or predicted, it can be stored in an electronic library of tooth shapes corresponding with the tooth type, as recited in step 28.

Figure 7:
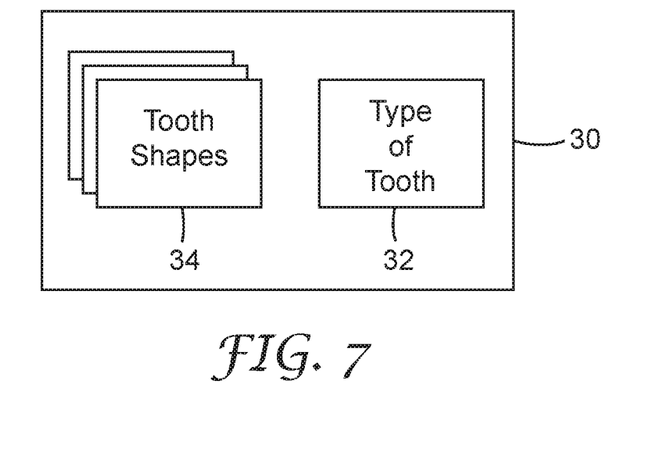
FIG. 7 is a diagram of a user interface illustrating display of tooth shapes corresponding with tooth types from a library of shapes.

FIG. 7 is a diagram of a user interface 30 illustrating display of tooth shapes corresponding with tooth types from a library of shapes. User interface 30 can be displayed on, for example, display device 16. User interface 30 can have a section 32 to display an indication of a type of tooth and a section 34 to display tooth shapes from the stored library corresponding with the shape identified in section 32.

Table 1 provides exemplary pseudocode for implementing the point classification (machine learning) training data algorithm. Table 2 provides exemplary pseudocode for implementing the point classification (machine learning) algorithm for tooth identification.

TABLE 1

Pseudocode for Machine Learning Training for Tooth Identification

Input: Multiple 3D meshes with a sets of vertices V specified in 3D coordinate system X, Y, and Z. The mesh also has a set of triangulations or faces F based on the vertices. Each mesh corresponds to an individual segmented tooth. Also the groundtruth labels in the form of the tooth type names as indicated by manual annotation.
Output: A predictive model that is capable of classifying each tooth mesh according to its tooth type.
Assumptions: Each individual mesh corresponds to an individual segmented tooth, without any gingiva.
Method steps:
  1  For each vertex in every mesh in the training set of data, compute the following features:
      a. Normal directions
      b. Absolute, mean, and Gaussian curvatures, and directions of maximum and minimum curvature
      c. Shape context
      d. Mesh fourier
      e. Spin image
      f. Mesh local covariance
      g. PCA features
  2  For each tooth mesh, aggregate the features over all vertices in that mesh to form a feature descriptor for the entire tooth mesh. This aggregation may be done by computing the vectorized log-covariance of all features across all vertices in the mesh. (An alternate aggregation approach may be used, such as histograms, or means, or others.)
  3  Construct a data matrix X which is M X N where M is the total number of segmented tooth meshes and N is the total number of feature dimensions from Step 2.
  4  Train a RUSBoosted decision tree classifier that can predict the labels corresponding to the tooth type. (An alternate classifier can be used.)

TABLE 2

Pseudocode for Machine Learning Prediction for Tooth Identification

Input: a 3D mesh with a set of vertices V specified in 3D coordinate system X, Y and Z. The mesh also has a set of triangulations or faces F based on the vertices. The mesh corresponds to an individual segmented tooth.
Output: Predicted or identified tooth type of the presented tooth.
Assumptions: The mesh corresponds to an individual segmented tooth without any gingiva.
Method steps:
  1  For each vertex $v_i$ in V, compute the following features:
      a. Normal directions
      b. Absolute, mean, and Gaussian curvatures, and directions of maximum and minimum curvature
      c. Shape context
      d. Mesh fourier
      e. Spin image
      f. Mesh local covariance
      g. PCA features
  2  Aggregate the features over all vertices in this mesh, to form a feature descriptor for the entire tooth mesh.
  3  Construct a data vector X which is N x 1 dimensional where N is the total number of feature dimensions from Step 2
  4  Predict using the learned decision tree RUSBoost classifier the label corresponding to the tooth type Contextual Information for Tooth Recognition The tooth identification in step 26 of method 22 of FIG. 4 can be refined or supplemented with contextual information (step 27) such as likelihood of co-occurrence of tooth types, along with the constraint of each patient case having only one tooth of each type in order to improve the accuracy of an individual tooth classification. Using the contextual information can enable near-perfect, or very high accuracy, tooth recognition and identification as measured in a patient-wise accuracy metric.

Given an input 3D scan of a patient's dental arch, the point classification of step 26 as described above uses 3D mesh features along with learned models of 3D tooth shapes to predict the tooth types of the individual teeth. In particular, each segmented tooth is passed to a tooth type classifier, which computes the covariance descriptor of 3D mesh features over the entire tooth shape, and classifies this feature to one of thirty-two tooth types based on the learned classification model. In the aforementioned approach, the individual teeth are being classified independently of each other. There is not necessarily any influence on a tooth's structure, location, and predicted tooth type on the predicted tooth types for the neighboring teeth, or any other teeth in that particular patient's mouth. However, since the teeth are arranged in a particular order, they can be considered as a chain-connected graph of mesh objects, where each object is an individual tooth. Based on this layout, the labels of individual teeth will affect the labels of adjacent teeth. If the independent tooth recognition algorithm provides as output probabilities of likely labels for a particular tooth, then the ranked ordering of likely labels can be used for further refinement. For example, if one tooth object is assigned a particular label with very high probability, it is equally highly unlikely that any other tooth in the mouth will be assigned that same label, meaning the probability of that label in the other teeth would be down-weighted. This contextual information can thus be used to develop rules to adjust the weighting of the predicted probability of tooth labels. For example, given a location of a particular tooth within an arch and the predicted labels of neighboring teeth, the predicted label (identification) of the particular tooth can be adjusted to refine the accuracy of the prediction.

Figure 8:
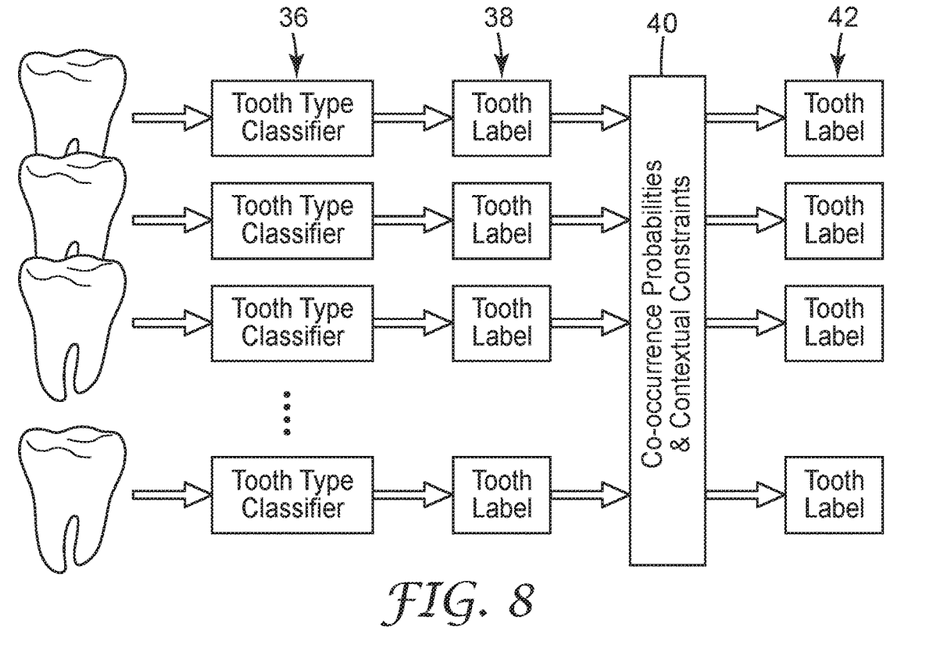
FIG. 8 is a diagram illustrating use of contextual information along with the classification method for tooth identification.

Therefore, this alternative tooth recognition or identification approach can be represented as shown in FIG. 8, where after the initial independent tooth type classifier provides its predicted labels (steps 36 and 38 as implemented by step 26 in method 22), the contextual information (step 40) is used to re-assigns the labels to obtain an improved or refined output of labels for the teeth (step 42) using the contextual factors described above.

Tooth Recognition without Segmentation

As represented by step 25 in method 22 of FIG. 4, tooth type recognition or identification can be performed without the requirement of segmentation. Given an input 3D scan of a patient's dentition (either a full arch or a partial arch), 3D mesh features are computed. Combining these features with the knowledge of probability distributions of typical tooth sizes and trained feature models that represent each individual teeth, this alternative method can estimate the most likely configuration of teeth in the provided arch. This estimate can also be used to guide tooth segmentation, which can further refine our tooth recognition, leading to an iterative process which provides highly accurate tooth segmentation and recognition.

Figure 9:
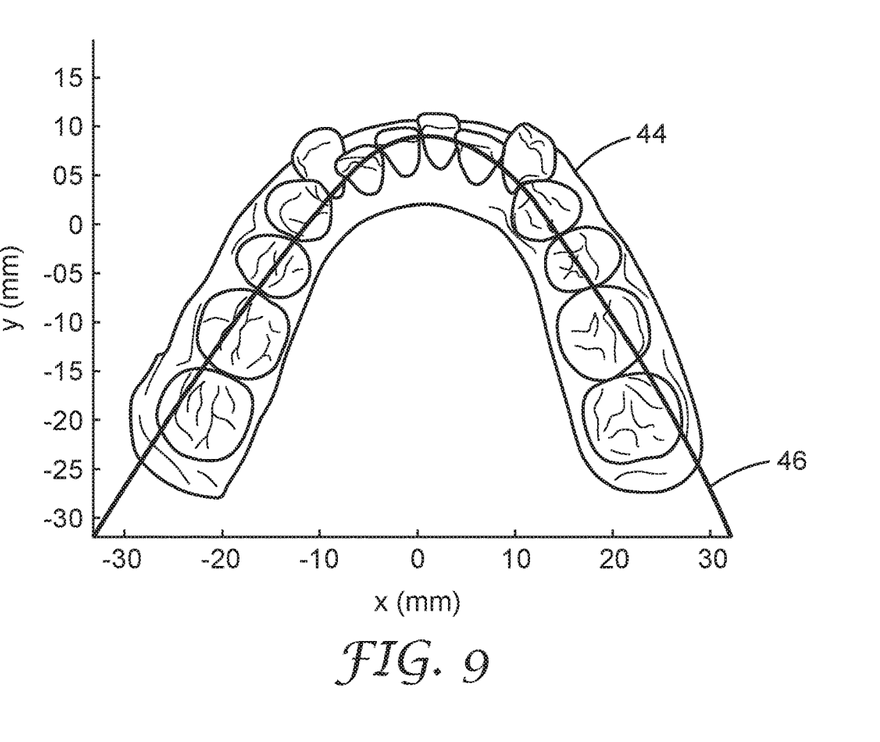
FIG. 9 is a diagram illustrating fitting a polynomial to vertices of a 3D scan for use in tooth identification without segmentation.

As shown in FIG. 9, given an input 3D mesh 44 (digital 3D model) of a patient's dentition (either a full arch or a partial arch), this tooth identification involve computing the length of the arch in millimeters (mm) or other unit by fitting a cubic polynomial 46 to the mesh vertices.

Based on a large training set of segmented teeth, the typical tooth widths are computed along the length of this arch curve. The average tooth widths can be obtained from publications, for example: Wheeler, Russell Charles, and Major M. Ash, *Wheeler's atlas of tooth form*, WB Saunders Company, 1984. The distribution of the typical number of teeth per patient case can also be computed. From this prior knowledge, this tooth identification can synthesize a variety of possibilities of teeth configurations that will satisfy the constraints imposed by the length of the patient's dental arch, and each configuration is assigned a probability of being the correct one. Table 3 provides a sample list of such configurations, ranked from the most likely to the least likely configuration.

TABLE 3

| Sample Configurations | |
|---|---|
| Configuration | Probability of Correctness |
| [LL7, LL6, LL5, . . . . , LR6, LR7] | 45% |
| [LL8, LL7, . . . , LR5, LR6] | 27% |
| . . . | |
| [LR8, LL8, LR6, . . . , UR5] | 0.0000001% |

From the dental mesh itself, this tooth identification can compute a variety of 3D shape features that describe the local shape variations. The tooth identification with segmentation described above computes the covariance of these features over all the vertices in an individual tooth. However, if the covariance of these features over the entire dental mesh ($C_M$) is computed, this can be related to the covariances of features of the individual teeth ($C_i$, where i=1, . . . , 32, corresponds to the tooth label) as follows:

$$C_M = \alpha_1 C_1 + \alpha_2 C_2 + \ldots + \alpha_{32} C_{32},$$

where $\alpha_1, \alpha_2, \ldots, \alpha_{32}$ represent the coefficients of linear combination as determined by the relative sizes and number of mesh vertices in each individual tooth.

The typical values for the individual tooth covariance $\{C_1, \ldots, C_{32}\}$ can be learned from a training set of covariance features from individual segmented teeth corresponding to each tooth type. These values can be put together to form a dictionary model of teeth covariance features. The dictionary model can have more than one covariance feature for each tooth type to account for large variations—for example, lower $1^{st}$ molars can be either 4-cusp or 5-cusp, which might yield different covariances—resulting in a dictionary of length much larger than the number of tooth types present.

When this method receives a new dental mesh, it computes the mesh covariance feature over the entire arch as $C_M$, and applies a technique called as tensor (or covariance) sparse coding to compute the coefficients $\{\alpha_1, \alpha_2, \ldots, \alpha_{32}\}$. The sparse coding approach will try to push as many of the coefficients as possible to zero, and therefore the non-zero coefficients would correspond to the teeth that are present. These coefficients can be correlated with the highly likely configurations of teeth mentioned earlier. In another way, the high likelihood tooth configurations can be used to guide the sparse coding approach by weighting the coefficients used to initialize the optimization problem.

Figure 10:
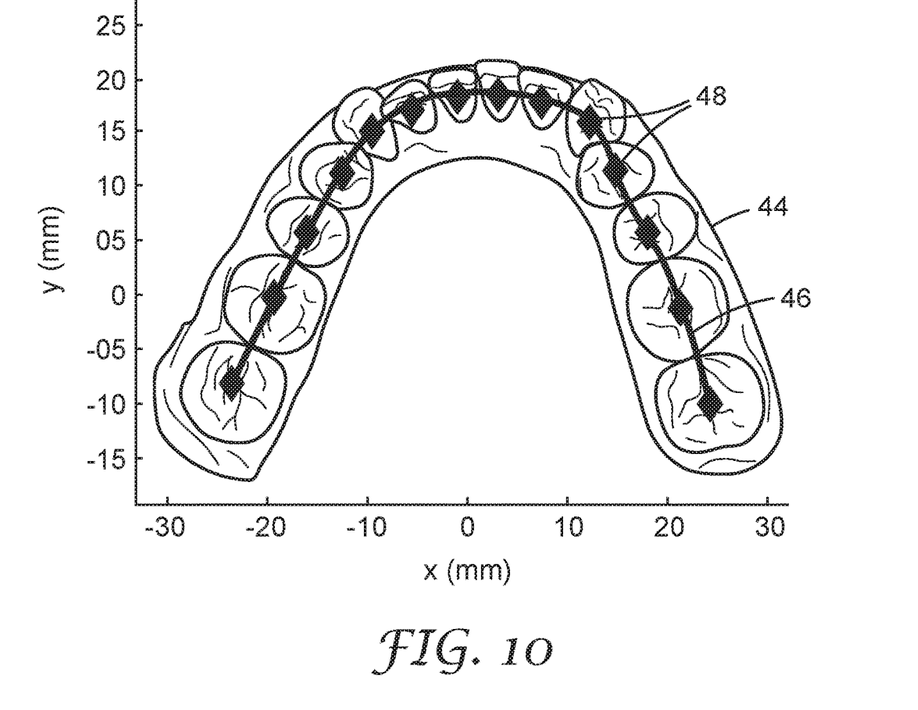
FIG. 10 is a diagram illustrating the 3D scan of FIG. 9 with the teeth identified and the polynomial sectioned by the teeth.

Based upon this sparse linear representation of the full arch covariance in terms of individual tooth covariance features, this alternative method can predict the labels of the teeth present in the given dental arch without resorting to segmentation. With the prior knowledge of tooth sizes, this information can be used to virtually divide the cubic polynomial arch form into sections as shown in FIG. 10, where the polynomial 46 on arch 44 has been divided as represented by points 48 on individual teeth. These sections can then also be used to initialize a tooth segmentation algorithm. The tooth type recognition and tooth segmentation can be an iterative process with the initial tooth recognition guiding segmentation, and the output segmented teeth being used to refine the predicted tooth types.

Figure 11:
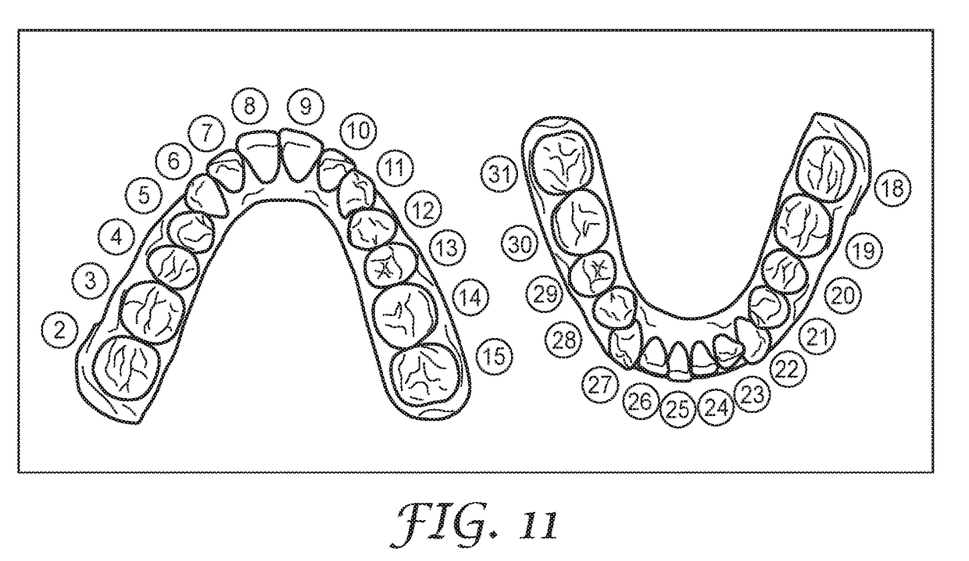
FIG. 11 is a diagram of a user interface illustrating a dental scan with tooth numbering for use in or representing automatic tooth identification.

FIG. 11 is a diagram of a user interface illustrating a digital 3D model of upper and lower arches of teeth along with numbers associated with each tooth in the model. Those numbers can be correlated with predicted types of each tooth in the model using any of the tooth identification or prediction methods described herein. The user interface in FIG. 11 can be displayed on, for example, display device 16.

Tooth Width Distributions for Segmentation

The following method involves an approach to use the distribution of tooth widths for each tooth type as a priori for tooth segmentation. When the dental status (list of teeth present) of the patient is known, this information can be used in conjunction with the typical tooth widths of those teeth to guide the sectioning of the dental arch into sections by interstitial planes. The interstitial planes are determined by local minima of lingual-labial widths along the dental arch. The challenges in identifying the interstitial planes accurately due to shape complexity of the posterior teeth (such as molars) and gingiva structure can be alleviated using this prior knowledge about tooth sizes.

Figure 12:
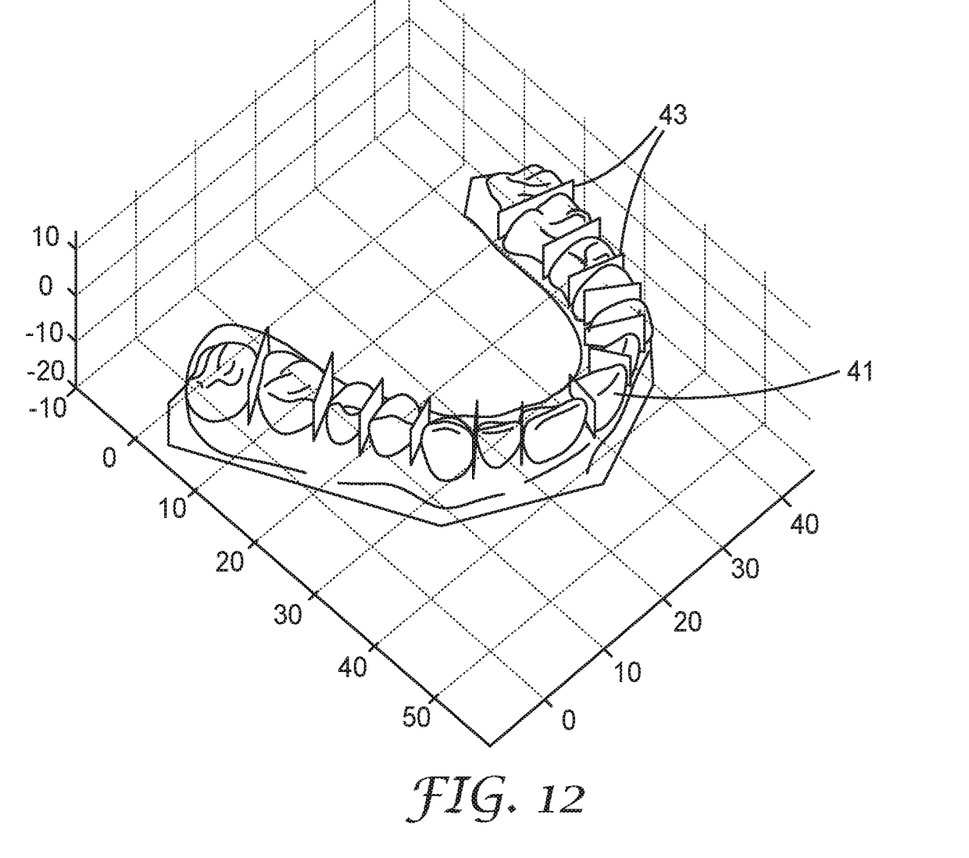
FIG. 12 is a diagram illustrating interstice detection on a 3D scan of an arch.

Teeth segmentation includes, as a key step for example, the detection of interstitial planes along the arch form of the dentition. The interstices are detected by taking the cross-section of the teeth along this arch form and finding local minima in the widths, which would correspond to gaps between individual teeth. FIG. 12 is a diagram illustrating interstice detection, represented by virtual planes 43, on a digital 3D model of an arch 41.

Usually, the scans of a patient's dentition are accompanied by the dental status provided by a dentist or orthodontist. In a given arch with the ordered list of teeth present, this method can use typical tooth widths along the arch based on prior data and concatenate them together, which can provide an initial estimate of where the interstices—the gaps between the individual teeth—are located. The typical tooth widths can be computed from a population sample, and this computation can include the average tooth widths for each tooth type as well as the corresponding variances, for example from the publication cited above.

Figure 13:
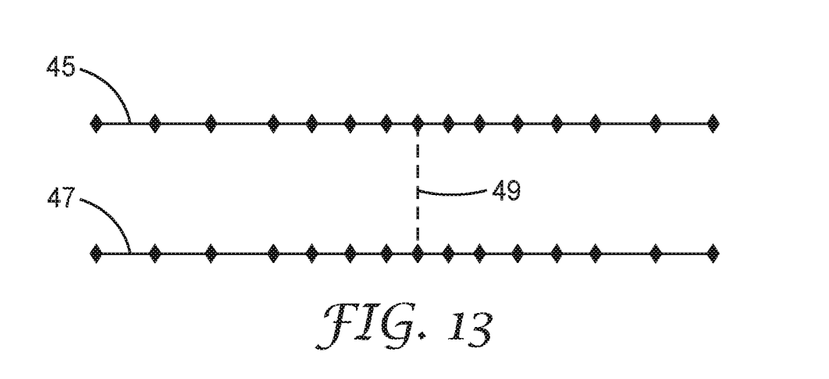
FIG. 13 is a diagram illustrating tooth widths concatenated on a straightened arch form.

The tooth widths of the teeth in the sample arch (as given by the dental status) can be concatenated and their sum normalized by the arch form length. FIG. 13 shows an unwrapped arch form 45—a linearized version of the arch curve with the interstices determined by the average tooth widths. The length of this arch line has been normalized to one. FIG. 13 also shows a similar line 47 derived from the interstices of the sample arch, as illustrated in FIG. 10. Lines 45 and 47 are concatenated as illustrated by line 49 connecting two interstices in the middle of the arches. As illustrated in FIG. 13, the canonical and sample arch lines 45 and 47 can be approximately within the standard deviation bounds specified by for average widths from a population sample.

Thus, the canonical arch form 45 intervals can be used on sample arch 47 to obtain an initial estimate of interstice plane locations. These initial estimates can then be refined to determine more accurate estimates of the interstices. This approach provides for the number of interstices detected corresponding to the number of teeth and also prevents interstices from being generated in the middle of complex shaped teeth, such as molars, or along raised gum lines behind the molars.

Figure 14:
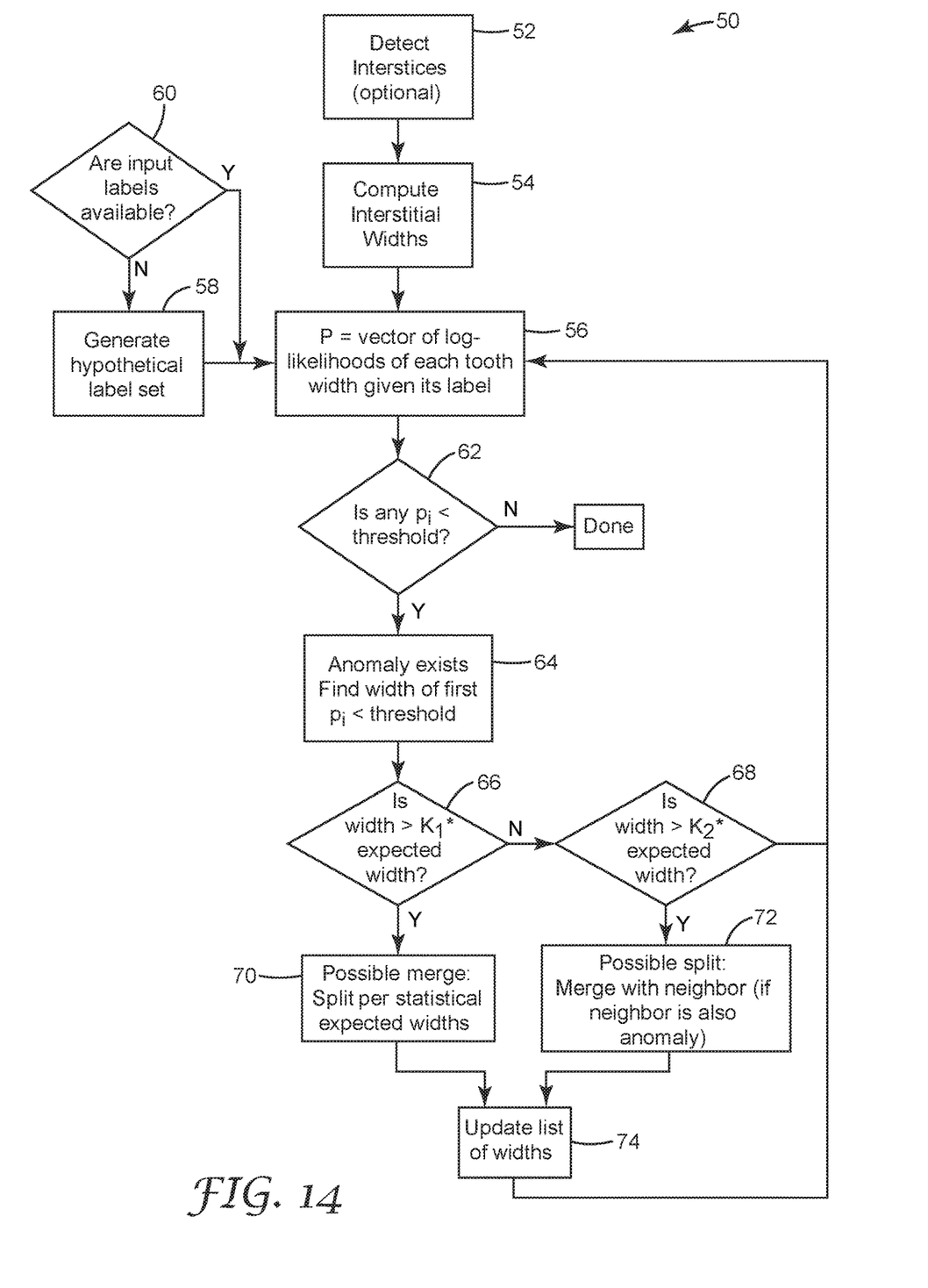
FIG. 14 is a flow chart of a method for using tooth width distributions to improve teeth segmentation in a 3D scan.

FIG. 14 is a flow chart of a method 50 for using tooth width distributions to improve teeth segmentation in a 3D scan. Method 50 can be implemented in software or firmware modules, for example, for execution by processor 20. Method 50 can alternatively be implemented in hardware modules or a combination of software and hardware.

Method 50 optionally detects interstices (step 52) and computes interstitial widths (step 54). Method 50 can receive input labels, if available (step 60) or generate a hypothetical label (step 58). The value p is calculated (step 56), where p=vector of log-likelihoods of each tooth width given its label.

If any $p_i$<threshold (step 62), an anomaly exists, and method 50 finds the width of the first $p_i$<threshold (step 64). If the width of $p_i$>$K_1$*expected width (step 66), then the method splits according to statistical expected widths as a possible merge (step 70). Otherwise, if the width>$K_2$*expected width (step 68), then the method merges with neighbor (if neighbor is also an anomaly) as a possible split (step 72). The list of widths is then updated (step 74). The coefficients $K_1$ and $K_2$ can vary for each type of tooth and be determined through empirical evidence or in other ways. For example, a $K_1$ of 110% can be used, meaning the width is 110% greater than the expected width, and a $K_2$ of 80% can be used, meaning the width is 80% less than the expected width. Other values of $K_1$ and $K_2$ can also be used. As a result, for each set of input labels (real or hypothetical) the sum of the log probabilities of the estimated widths based on method 50 is stored. Eventually, the set of widths corresponding to the highest sum of log likelihood values is obtained and can be used for segmentation of the digital 3D model of the teeth or for other purposes.

Figure 15:
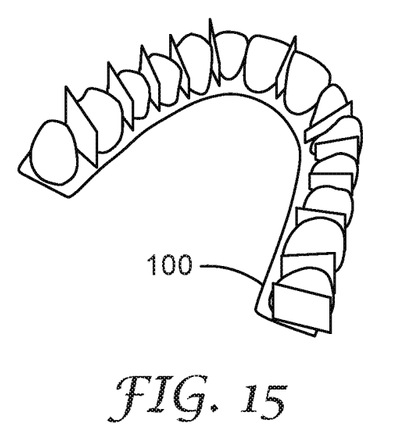
FIG. 15 illustrates a 3D model of teeth before a split function of interstice detection.
Figure 16:
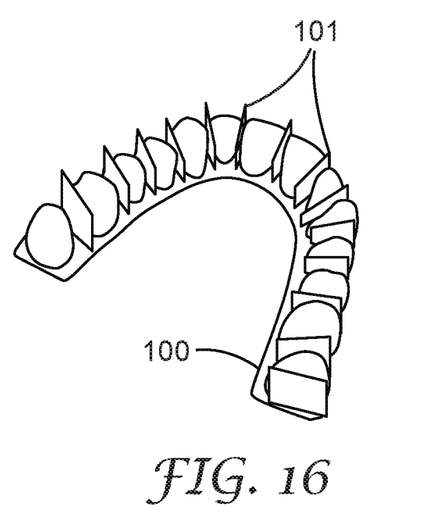
FIG. 16 illustrates a 3D model of teeth after a split function of interstice detection.
Figure 17:
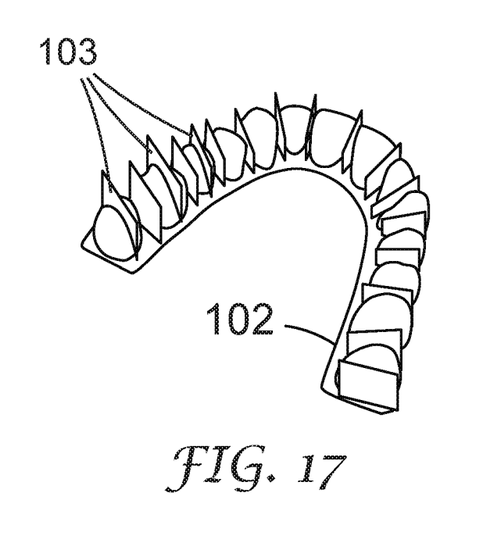
FIG. 17 illustrates a 3D model of teeth before a merge function of interstice detection.
Figure 18:
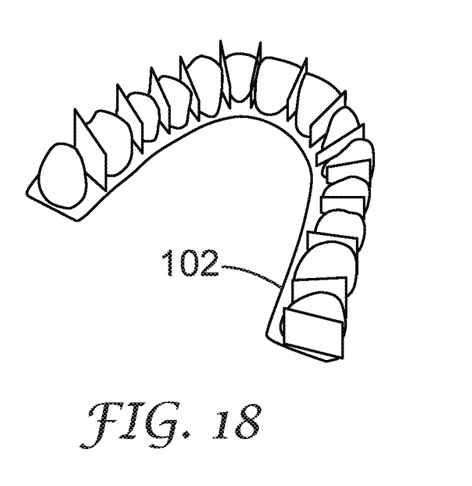
FIG. 18 illustrates a 3D model of teeth after a merge function of interstice detection.

The split and merge functions of steps 70 and 72 are illustrated in FIGS. 15-18. FIGS. 15 and 16 illustrate, respectively, a 3D model of teeth 100 before and after a split function of interstice detection where extra interstices, virtual planes 101, have been added to separate teeth in the model. FIGS. 17 and 18 illustrate, respectively, a 3D model of teeth 102 before and after a merge function of interstice detection where particular interstices, in this case virtual planes 103, have been removed to join portions of individual teeth.

The invention claimed is:

1. A computer-implemented method for identifying a tooth type, comprising steps of:

receiving, executed by a processor, a digital 3D model of an arch of teeth, wherein actual types of the teeth are not identified;

determining, executed by the processor, widths of teeth within the digital 3D model of the arch;

identifying, executed by the processor, types of teeth in the digital 3D model of the arch with a particular degree of accuracy of the actual types of the teeth based upon the determined widths and locations of the teeth in the arch; and detecting, executed by the processor, interstices between teeth within the digital 3D model of the arch using the determined widths, wherein the detecting step further comprises, executed by the processor, determining if a detected one of the interstices has a width greater than an expected width by a particular amount.

2. The method of claim 1, wherein the identifying step comprises comparing the determined widths with average tooth widths.

3. The method of claim 1, wherein the detecting step comprises comparing the determined widths with average tooth widths.

4. The method of claim 1, further comprising, executed by the processor, providing markings within the digital 3D model of the arch, wherein the markings correspond with the detected interstices.

5. A computer-implemented method for identifying a tooth type, comprising steps of:
receiving, executed by a processor, a digital 3D model of an arch of teeth, wherein actual types of the teeth are not identified;
determining, executed by the processor, widths of teeth within the digital 3D model of the arch;
identifying, executed by the processor, types of teeth in the digital 3D model of the arch with a particular degree of accuracy of the actual types of the teeth based upon the determined widths and locations of the teeth in the arch; and
detecting, executed by the processor, interstices between teeth within the digital 3D model of the arch using the determined widths,
wherein the detecting step further comprises, executed by the processor, determining if a detected one of the interstices has a width less than an expected width by a particular amount.

6. The method of claim 1, wherein the receiving step comprises receiving the digital 3D model of the arch unsegmented.

7. The method of claim 1, wherein the identifying step comprises comparing the determined widths and locations of the teeth in the arch with known configurations of average tooth widths.

8. A computer-implemented method for identifying a tooth type, comprising steps of:
receiving, executed by a processor, a digital 3D model of an arch of teeth, wherein actual types of the teeth are not identified;
determining, executed by the processor, widths of teeth within the digital 3D model of the arch;
identifying, executed by the processor, types of teeth in the digital 3D model of the arch with a particular degree of accuracy of the actual types of the teeth based upon the determined widths and locations of the teeth in the arch; and
displaying, executed by the processor, within a user interface the digital 3D model of teeth within the arch and numbers associated with each tooth within the arch, wherein the numbers are correlated with the identified types of each tooth within the arch.

9. The method of claim 4, wherein the providing step comprises providing virtual planes as the markings.

10. The method claim 1, further comprising, executed by the processor, segmenting teeth within the digital 3D model of the arch based upon the detected interstices.

11. The method of claim 5, wherein the identifying step comprises comparing the determined widths with average tooth widths.

12. The method of claim 5, wherein the detecting step comprises comparing the determined widths with average tooth widths.

13. The method of claim 5, further comprising, executed by the processor, providing markings within the digital 3D model of the arch, wherein the markings correspond with the detected interstices.

14. The method of claim 13, wherein the providing step comprises providing virtual planes as the markings.

15. The method of claim 5, wherein the receiving step comprises receiving the digital 3D model of the arch unsegmented.

16. The method of claim 5, wherein the identifying step comprises comparing the determined widths and locations of the teeth in the arch with known configurations of average tooth widths.

17. The method claim 5, further comprising, executed by the processor, segmenting teeth within the digital 3D model of the arch based upon the detected interstices.

18. The method of claim 8, wherein:
the receiving step comprises receiving upper and lower arches of teeth; and
the displaying step comprises displaying the upper and lower arches of the teeth with the numbers.

* * * * *

UNITED STATES PATENT AND TRADEMARK OFFICE
CERTIFICATE OF CORRECTION

PATENT NO. : 10,916,008 B2  
APPLICATION NO. : 16/018115  
DATED : February 9, 2021  
INVENTOR(S) : Guruprasad Somasundaram Page 1 of 1

It is certified that error appears in the above-identified patent and that said Letters Patent is hereby corrected as shown below:

In the Specification

Column 3  
Line 32, delete "28)" and insert -- 28). --, therefor.

Column 4  
Line 51, after "is" insert -- the --.  
Line 53, delete "as" and insert -- as: --, therefor.

In the Claims

Column 12  
Line 15, in Claim 10, after "method" insert -- of --.  
Line 37, in Claim 17, after "method" insert -- of --.

Signed and Sealed this  
Thirteenth Day of April, 2021

Drew Hirshfeld  
*Performing the Functions and Duties of the*  
*Under Secretary of Commerce for Intellectual Property and*  
*Director of the United States Patent and Trademark Office*